United States Patent [19]
Zahn

[11] 4,205,442
[45] Jun. 3, 1980

[54] DENTAL STRESS-RELIEVING APPARATUS

[75] Inventor: Eric H. Zahn, Bellevue, Wash.

[73] Assignee: Sterndent Corp., Old Greenwich, Conn.

[21] Appl. No.: 897,585

[22] Filed: Apr. 19, 1978

[51] Int. Cl.² ............................................. A61C 13/22
[52] U.S. Cl. ................................................. 433/170
[58] Field of Search ............................................ 32/5, 7

[56] References Cited
U.S. PATENT DOCUMENTS

| | | | |
|---|---|---|---|
| 2,611,957 | 9/1952 | Baca et al. | 32/7 |
| 2,797,456 | 7/1957 | Zahn | 32/5 |
| 3,057,068 | 10/1962 | Morandi | 32/5 |
| 3,388,471 | 6/1968 | Thompson | 32/7 |
| 3,434,526 | 3/1969 | Prosen | 32/7 |

FOREIGN PATENT DOCUMENTS 276547 10/1951 Fed. Rep. of Germany ................ 32/7

*Primary Examiner*—Russell R. Kinsey
*Assistant Examiner*—Michael J. Foycik, Jr.
*Attorney, Agent, or Firm*—Ford E. Smith; David L. Garrison

[57] ABSTRACT

A two-part stress-reliever employs a first member supporting an upright flange and a second member bifurcated and straddling said flange. An elongated slot in the flange receives a pass-through pivot pin carried by the second member and said slot also includes a resilient body biasing the pivot pin to its normal unstressed position in said slot.

7 Claims, 7 Drawing Figures

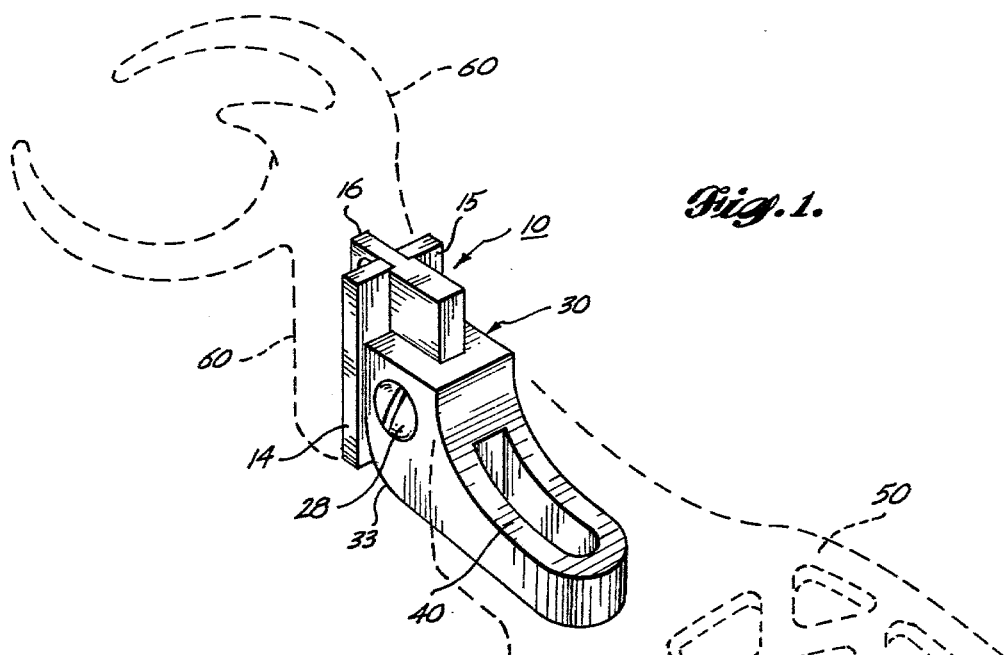
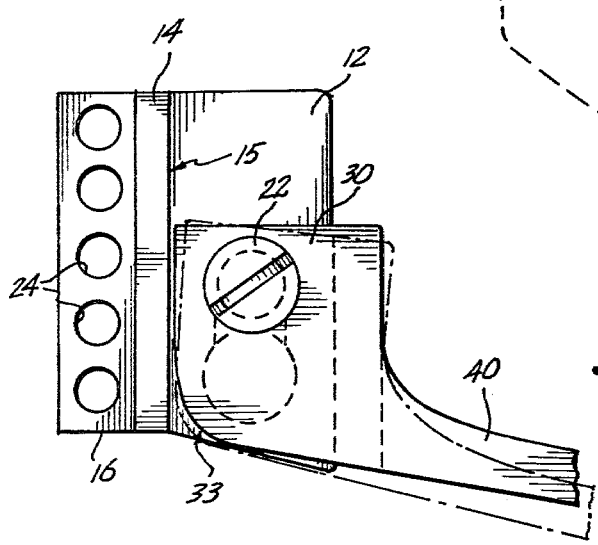
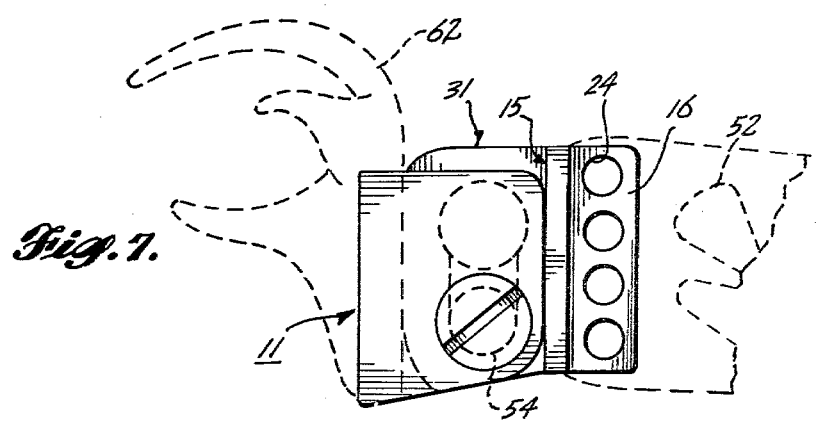

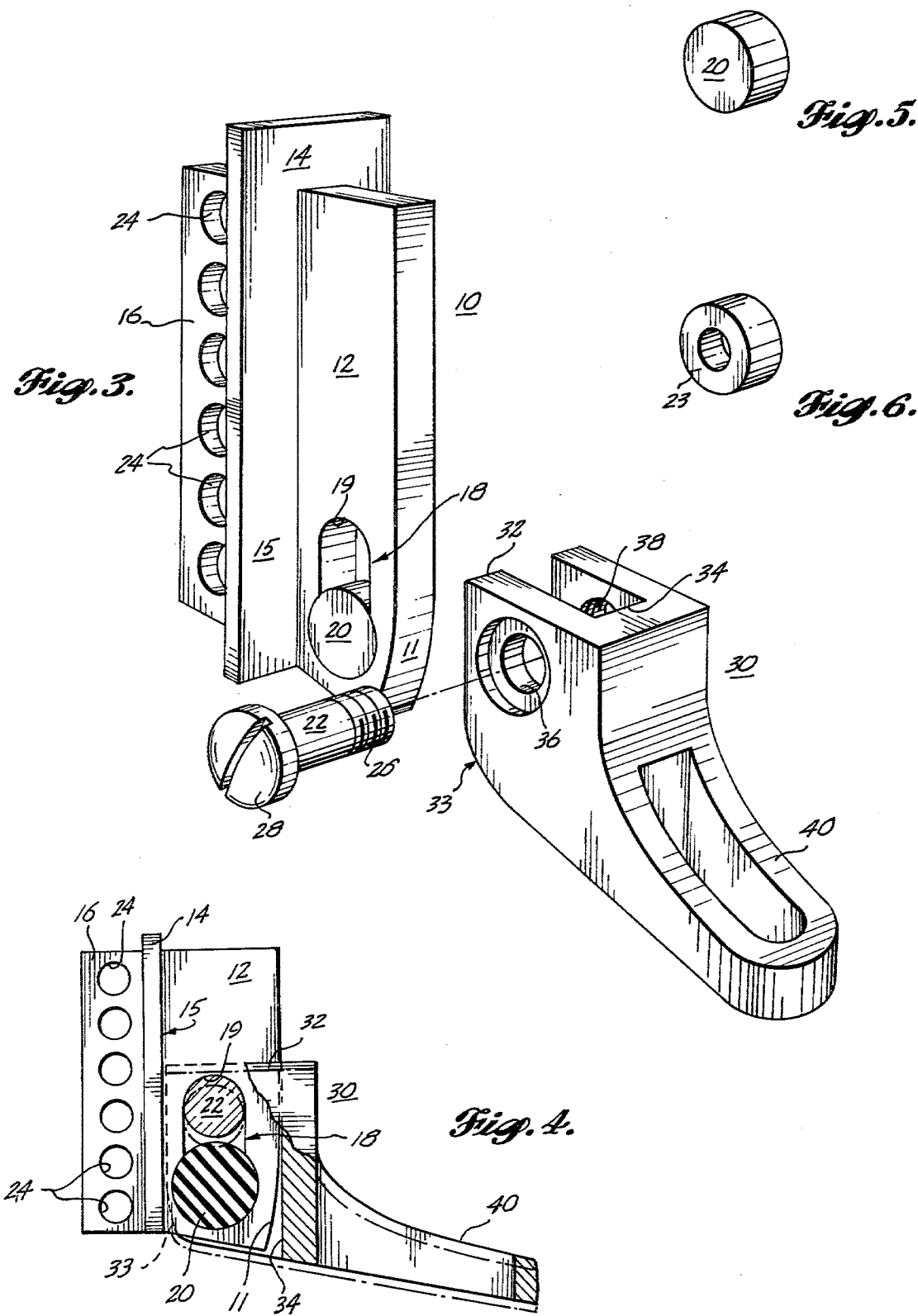

_(4,205,442)_

DENTAL STRESS-RELIEVING APPARATUS

PRIOR ART STATEMENT

Prior patent art currently known to applicant comprises:
U.S. Pat. No. 2,611,957—9/1952—Baca et al.
U.S. Pat. No. 2,797,456—7/1957—Zahn The relevancy of this prior art is considered limited to the extent that bifurcated members are pivotally pinned to a flange-like member which may also be slotted to permit relative sliding or slipping movement. These disclosures are devoid of any resilient biasing system.

SUMMARY OF THE INVENTION

It is a primary object of this invention to provide stress-relieving apparatus for use in the production of dental partial restorations in which both pivoting and longitudinal movement between anchor means and tooth-carrying means are supplied and the longitudinal movement is under conditions of bias and in an axis generally parallel to the primary anchor tooth axis.

DESCRIPTION OF THE DRAWINGS

FIG. 1 is a perspective view of the stress reliever of this invention showing in phantom lines parts of dental restoration apparatus with which the stress reliever is incorporated for use;

FIG. 2 is a side view of the stress reliever indicating its microdimensions;

FIG. 3 is an exploded perspective view showing the various parts of the stress reliever;

FIG. 4 is a side view of the stress reliever unit with portions broken away to facilitate comprehension;

FIGS. 5 and 6 are perspective view of two forms of resilient members; and

FIG. 7 is a side view of the stress reliever showing an alternate mode of incorporating the same into a dental restoration.

DESCRIPTION OF A PREFERRED EMBODIMENT

Referring to the exploded perspective view of FIG. 3, the stress reliever comprises the flange member 10 and the bifurcated member 30. Member 10 includes upright flange 12, face plate 14 and rearstanding flange 16. The lower portion of flange 12 is provided with a pass-through slot 18 which here is shown as an inverted key-hole shaped opening. Slot 18 is sized at one end to receive the cylindrical resilient disc 20 and the shank pivot pin 22 passes through the other end. Rear flange 16 includes perforations 24.

An alternate form of resilient member 23 is shown in FIG. 6 as a hollow cylinder or tube. Members 20 and 23 may have their resiliency controlled not only by being solid or hollow but by varying their compression or their hardness on the Durometer scale. In any event, members 20 or 23 snugly occupy an end portion of opening 18 and tend to bias pin 22 toward its usual position as its movement may cause it to bear on and compress the adjacent resilient member. When not under pressure, pin 22 usually is freely rotatable in that end of the slot away from the opposing resilient member 20 or 23.

Continuing with reference to FIG. 3, the bifurcated or forked member 30 includes fork arms 32, 32 forming a throat having sides spaced apart sufficiently to receive flange 12. The gullet 34 in the assembly is juxtaposed closely to edge 13 of flange 12. The lower end 11 of flange 12 is cut away and relieved as shown. Likewise the lower ends of arms 32, 32 are relieved at 33. When member 30 straddles flange 12, pin 22 passes through hole 36, the opening 18 and into hole 38. Head 28 is seated preferably flush in the countersink recess 37 at the entrance to hole 36 and the pin threads 22 and 26 engage in matching threads provided in hole 38.

It will be apparent that, when the parts shown in FIG. 3 are assembled as in FIGS. 1, 2 and 4, bifurcated member 30 and flanged member 10 may be relatively pivoted in one direction and that member 30 may move longitudinally of flange member 10 or vice versa. When such longitudinal movement under pressure occurs, as indicated in dashed lines in FIG. 4, the pivot pin moves into space occupied by biasing resilient member 20 or 23. When pressure is relieved, the resilient member 20 or 21 tends to force pin 22 back into opening portion 19 of slot 18. It should be understood that slot 18 may have parallel sides and ends of the same curvature.

Pivoting movement between parts 10 and 13 is easily controlled by a dental technician by the amount of relief he provides at 11 or 33. This is best understood by reference to FIG. 4. Those portions 33 of arms 32 that bear on the face 15 of face plate 14 and that portion of flange 11 that comes to bear on the lower portion of gullet 34 limit pivotal movement and the degree to which parts of a dental restoration attached to either may move relative the other. Such movement is indicated by solid and dashed lines in FIG. 2 and is usually quite slight, sufficient to relieve stress on an anchor tooth as one engaged by clasp 60.

Member 30 includes the U-shaped arm 40, extending from the bifurcated member 30. Arm 40 has a port 41. In the process of waxing-up a dental model and casting, the added parts, such as, a saddle member 50 shown in FIG. 1 or a clasp member 52 shown in FIG. 7, become joined to stress reliever parts 10 and 30.

In the preferred form of the invention, bifurcated member 30 carries ported arm 40 which aides its being securely incorporated into the saddle member 50 that ultimately supports the restoration teeth of a partial denture. In such case, the flange member 10, aided by perforations 24 in rear flange 16, is incorporated into a clasp 60. The incorporation of these parts 10 and 30 occurs as a result of the waxing-up and of the casting processes conventionally and usually employed by dental technicians or dentists in this art.

Alternatively, as shown in FIG. 7, the bifurcated member 11 may be incorporated into a clasp 62 and the flange member 31 is incorporated into saddle member 52. In such alternate arrangement, the disposition of the opening in the flange of member 31 is reversed and the resilient member overlies the pivot pin 54 rather than underlies it as in FIG. 4.

Flange member 10 is shown overlong throughout. It will be understood that its height will usually be reduced by a technician as circumstances dictate during production of the restoration. Member 10 is to be mounted so that the axis of slot 18 parallels the axis of the adjacent anchor tooth engaged by clasp 60.

With reference to FIG. 2, dimensions are indicated to give an inkling of the miniscule size of the preferred forms of this stress relieving apparatus, to wit:
A is about 0.250" high
B is about 0.125" wide C is about 0.135" high D is about 0.300" long It is very important that the fit of bifurcated member 30 to flange 12 be close, to within 0.001" to 0.003" for example. This has become possible by surface grinding the faces of flange 12 to desired dimensions and broaching or otherwise sizing the spacing of the arms of member 30 accordingly.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the legitimate and valid scope of the appended claims, appropriately interpreted in accordance with the doctrine of equivalents.

Having thus described the invention, what is claimed is:

1. Means for forming a stress reliever between anchor means of dental restoration apparatus and the saddle section thereof, comprising:

a flange member rigidly incorporated in upright disposition with one of said restoration sections;

a bifurcated member disposed to straddle said flange member and being rigidly incorporated with said other restoration section;

a pivot pin passing through said bifurcated member and said flange;

said bifurcated member and said flange member being adapted for relative pivotal movement about the axis of said pin; and a cavity in said flange adjacent said pin and communicating with the passage to permit relative longitudinal movement between said flange member and said bifurcated member, said cavity being occupied by resilient material operable to compress upon pressure tending to displace said pin from its normal disposition into said cavity and to bias said pin toward said passage.

2. The structure according to claim 1 in which the flange is rigidly incorporated with the clasp section and the bifurcated member is rigidly incorporated with the restoration saddle section.

3. The structure according to claim 1 in which the cavity is essentially cylindrical and a cylindrical member of resilient material occupies the same.

4. The structure according to claim 3 in which the cylindrical member has an axial passage.

5. The structure according to claim 3 in which the cylindrical member is solid.

6. The structure according to claim 3 in which said member is under compression.

7. The structure according to claim 1 in which there is a base plate contiguous with and standing normal to each side of said flange and juxtaposed to portions of the bifurcated member.

* * * * *